United States Patent
Hasegawa et al.

(10) Patent No.: US 10,390,017 B2
(45) Date of Patent: Aug. 20, 2019

(54) COMPRESSED IMAGE DATA TRANSMITTING DEVICE, COMPRESSED IMAGE DATA TRANSMITTING AND RECEIVING SYSTEM, COMPRESSED IMAGE DATA TRANSMITTING METHOD, AND NON-TRANSITORY MEDIUM SAVING PROGRAM

(71) Applicant: OLYMPUS CORPORATION, Hachioji-shi, Tokyo (JP)

(72) Inventors: Yasuhiro Hasegawa, Hanno (JP); Shunsuke Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 73 days.

(21) Appl. No.: 15/810,580

(22) Filed: Nov. 13, 2017

(65) Prior Publication Data

US 2018/0070086 A1 Mar. 8, 2018

Related U.S. Application Data

(63) Continuation of application No. PCT/JP2015/064059, filed on May 15, 2015.

(51) Int. Cl.
*H04N 7/18* (2006.01)
*H04N 19/127* (2014.01)
(Continued)

(52) U.S. Cl.
CPC ........ *H04N 19/127* (2014.11); *A61B 1/00011* (2013.01); *A61B 1/00016* (2013.01);
(Continued)

(58) Field of Classification Search
CPC .... H04N 19/127; H04N 19/132; H04N 19/13; H04N 19/152; H04N 5/23206;
(Continued)

(56) References Cited

U.S. PATENT DOCUMENTS

2003/0043263 A1* 3/2003 Glukhovsky ............ A61B 1/04
348/61
2003/0060734 A1* 3/2003 Yokoi ................ A61B 1/00156
600/593

(Continued)

FOREIGN PATENT DOCUMENTS

JP 5616017 B2 10/2014
WO 2006/100671 A2 9/2006

OTHER PUBLICATIONS

International Search Report dated Jul. 7, 2015, issued in counterpart application No. PCT/JP2015/064059, w/English translation. (7 pages).

*Primary Examiner* — Howard D Brown, Jr.
(74) *Attorney, Agent, or Firm* — Westerman, Hattori, Daniels & Adrian, LLP

(57) ABSTRACT

A compressed image data transmitting device includes a compression unit dividedly reading captured image data from an image capturing element a plurality of times and performing a compression process on the captured image data to generate compressed image data; a determining unit determining whether a compressed image data occupancy ratio is equal to or larger than a predetermined threshold value; and a control unit instructing the compression unit to stop reading the captured image data when the compressed image data occupancy ratio is equal to or larger than the predetermined threshold value. When the captured image data which has not been read from the compression unit is present in the image capturing element, the control unit instructs the image capturing element not to perform the image capturing, and subsequently instructs the image capturing element to perform the image capturing operation after the above-mentioned captured image data is no longer present.

8 Claims, 11 Drawing Sheets

(51) Int. Cl.
  *H04N 5/225*   (2006.01)
  *H04N 19/13*   (2014.01)
  *H04N 19/152*  (2014.01)
  *H04N 19/172*  (2014.01)
  *A61B 1/00*    (2006.01)
  *A61B 1/04*    (2006.01)
  *H04N 5/232*   (2006.01)
  *H04N 5/38*    (2006.01)
  *A61B 1/045*   (2006.01)
  *H04N 19/132*  (2014.01)

(52) U.S. Cl.
  CPC .............. *A61B 1/041* (2013.01); *A61B 1/045* (2013.01); *H04N 5/225* (2013.01); *H04N 5/23206* (2013.01); *H04N 5/38* (2013.01); *H04N 19/13* (2014.11); *H04N 19/132* (2014.11); *H04N 19/152* (2014.11); *H04N 19/172* (2014.11); *H04N 2005/2255* (2013.01)

(58) Field of Classification Search
  CPC ........ H04N 19/172; H04N 5/38; H04N 5/225; H04N 2005/2255; A61B 1/00011; A61B 1/041; A61B 1/00016; A61B 1/045
  See application file for complete search history.

(56) References Cited

U.S. PATENT DOCUMENTS

| | | | |
|---|---|---|---|
| 2005/0159643 A1* | 7/2005 | Zinaty | A61B 1/041 600/109 |
| 2006/0262186 A1* | 11/2006 | Avni | A61B 1/00016 348/65 |
| 2007/0299301 A1 | 12/2007 | Uchiyama et al. | |
| 2013/0271585 A1* | 10/2013 | Khan | H04N 5/23241 348/65 |
| 2018/0136456 A1* | 5/2018 | Watanabe | A61B 1/05 |

* cited by examiner

COMPRESSED IMAGE DATA TRANSMITTING DEVICE, COMPRESSED IMAGE DATA TRANSMITTING AND RECEIVING SYSTEM, COMPRESSED IMAGE DATA TRANSMITTING METHOD, AND NON-TRANSITORY MEDIUM SAVING PROGRAM

BACKGROUND OF THE INVENTION

Field of the Invention

The present invention relates to a compressed image data transmitting device, a compressed, image data transmitting and receiving system, a compressed, image data transmitting method, and a non-transitory medium saving program.

This application is a continuation application based on a PCT International Application No. PCT/JP2015/064059, filed on May 15, 2015. The content of the PCT International Application is incorporated herein by reference.

Description of Related Art

In the related art, an endoscope is widely used as a medical observation device that is introduced into the body of a subject such as a patient, to observe the inside of the body cavity. Moreover, in recent years, a swallowable endoscope (a capsule endoscope) including a photographing device and a communication device accommodated in a capsule-type housing has been developed, wherein the communication device is configured to wirelessly transmit image data captured by the photographing device to the outside of the body, and the like. The capsule endoscope has a function of moving through the inside of internal organs such as the esophagus, the stomach, the small intestine, the large intestine, or the like according to peristaltic movement thereof and sequentially taking photographs for the observation of the inside of the body cavity, after the endoscope is swallowed through the mouth of a patient and until the endoscope is naturally discharged from the human body.

During the movement of the capsule endoscope through the body cavity, the image data captured in the body cavity by the capsule endoscope is sequentially transmitted to the outside of the body by wireless communication, and the image data is accumulated in a memory provided inside or outside of an external terminal or displayed on a display provided in the external terminal as an image. The image data accumulated in the memory is imported into an information processing device via a cradle into which the external terminal is inserted, and a doctor or a nurse can perform diagnosis on the basis of an image displayed on a display of the information processing device or an image received and displayed on a display provided in the external terminal.

Image data is sometimes compressed as compressed image data and the compressed image, data is transmitted in order to cope with high-speed movement of a capsule endoscope and to realize a higher frame rate. Particularly, since a relatively high compression rate can be obtained in at variable-length code compression scheme which is a compression scheme in which an image data size after compression changes according to an original image, a high frame rate can be realized. However, when a variable-length code compression scheme is employed, the image data size after compression depends on the input image such that the image data size after compression may be larger than expected and the image data size may exceed the amount of data that a transmitter can wirelessly transmit in a unit transmission time, thus image loss may occur.

In order to prevent such a situation, a capsule endoscope, that increases a data compression rate when the occupancy ratio of a transmission buffer is high to prevent an overflow of the transmission buffer such that images can be transmitted reliably has been proposed (for example, see Japanese Patent No. 5616017).

SUMMARY OF THE INVENTION

According to a first aspect, of the present invention, a compressed image data transmitting device includes an image capturing element that captures images at a predetermined cycle and the image capturing element generates captured image data; a compression unit that dividedly reads one frame of the captured image data from the image capturing element a plurality of times and the compression unit performs a compression process on the captured image data to generate compressed image data; a transmitter that wirelessly transmits the compressed image data at a fixed bitrate; a transmission buffer that receives the compressed image data input from the compression unit, the transmission buffer stores the compressed image data, and the transmission buffer outputs the compressed image data to the transmitter; a determining unit that determines whether a compressed image data occupancy ratio is equal to or larger than a predetermined threshold value, the compressed image data occupancy ratio indicating a ratio of an area in which the compressed image data is being stored to an area of the transmission buffer in which the compressed image data is capable of being stored; and a control unit that instructs the compression unit to stop reading the captured image data when the compressed image data occupancy ratio is equal to or larger than the predetermined threshold value, wherein the compression unit generates the compressed image data according to a variable-length compression scheme in which fixed-length data is input and variable-length data is output, wherein the control unit instructs the image capturing element to perform an image capturing operation, and when the captured image data which has not been read from the compression unit is present in the image capturing element, the control unit instincts the image capturing element not to perform the image capturing operation, and the control unit subsequently instructs the image capturing element, to perform the image capturing operation after the captured image data which has not been read from the compression unit is no longer present in the image capturing element, wherein the transmission buffer stores the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein when the compressed image data occupancy ratio is equal to or larger than the predetermined threshold value and the reading of the captured image data has not been completed for predetermined lines of the image capturing element, the control unit delays a timing of stopping reading of the captured image data until the reading of the captured image data is completed for the predetermined lines.

According to a second aspect of the present invention, in the compressed image data transmitting device according to the first aspect, the control unit may stop reading of the captured image data during a predetermined period from a timing when the compressed image data occupancy ratio is equal to or larger than the predetermined threshold value, and the control unit may restart reading of the captured image data after the predetermined period has elapsed.

According to a third aspect of the present invention, in the compressed image data transmitting device according to the first aspect, the control unit may instruct the compress unit to perform the reading of the captured image data by the predetermined lines, the predetermined lines corresponding to the amount of data of the captured image data that the compression unit reads at one time.

According to a fourth aspect of the present invention, in the compressed image data transmitting device according to the third aspect, the control unit may instruct the compress unit to perform the reading of the captured image data at a predetermined cycle.

According to a fifth aspect of the present invention, in the compressed image data transmitting device according to the fourth aspect, the image capturing element may perform the image capturing operation at fixed time periods, and when the control unit stops reading of the captured image data during a period in which the compression unit reads one frame of the captured image data, the control unit may stop the image capturing operation of the image capturing element at an image capturing timing according to the fixed time periods and the control unit may instruct the image capturing element to perform the image capturing operation at the image capturing timing which is an integer multiple of the fixed time periods after the reading of the one frame of the captured image data is completed.

According to a sixth aspect of the present invention, a compressed image data transmitting and receiving system includes a compressed image data transmitting device and a compressed image data receiving device, wherein the compressed image data transmitting device includes an image capturing element that captures images at a predetermined cycle and the image capturing element generates captured image data, a compression unit that dividedly reads one frame of captured image data from the image capturing element a plurality of times and the compression unit performs a compression process on the captured image data to generate compressed image data, a transmitter that is wirelessly transmits the compressed image data at a fixed bitrate, a transmission buffer that receives the compressed image data input from the compression unit, the transmission buffer stores the compressed image data, and the transmission buffer outputs the compressed image data to the transmitter, a determining unit that determines whether a compressed image data occupancy ratio is equal to or larger than a predetermined threshold value, the compressed image data occupancy ratio indicating a ratio of an area in which the compressed image data is being stored to an area of the transmission buffer in which the compressed image data is capable of being stored, and a control unit that instructs the compression unit to stop reading the captured image data when the compressed image data occupancy ratio is equal to or larger than the predetermined threshold value, wherein the compression unit generates the compressed image data according to a variable-length compression scheme in which fixed-length data is input and variable-length data is output, wherein the control unit instructs the image capturing element to perform an image capturing operation, and when the captured image data which has not been read from the compression unit is present in the image capturing element, the control unit instructs the image capturing element not to perform the image capturing operation, and the control unit subsequently instructs the image capturing element to perform the image capturing operation after the captured image data which has not been read from the compress ion unit is no longer present in the image capturing element, wherein the transmission buffer stores the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein when the compressed image data occupancy ratio is equal to or larger than the predetermined threshold value and the reading of the captured image data has not been completed for predetermined lines of the image capturing element, the control unit delays a timing of stopping reading of the captured image data until the reading of the captured image data is completed for the predetermined lines; and wherein the compressed image data receiving device includes a receiver that wirelessly receives the compressed image data from the compressed image data transmitting device at a fixed bitrate.

According to an seventh aspect of the present invention, a compressed image data transmitting method includes an image capturing step of capturing images at a predetermined cycle and generating captured image data by an image capturing element; a compression step of dividedly reading one frame of the captured image data input from the image capturing element a plurality of times and performing a compression process on the captured image data to generate compressed image data by a compression unit; a transmitting step of wirelessly transmitting the compressed image data at a fixed bitrate by a transmitter; a transmission buffering step of receiving the compressed image data from the compression unit, storing the compressed image data, and output ting the compressed image data to the transmitter by a transmission buffer; a determining step of determining whether a compressed image data occupancy ratio is equal to or larger than a predetermined threshold value by a determining unit, the compressed image data occupancy ration indicating a ratio of an area in which the compressed image data is being stored to an area of the transmission buffer in which the compressed image data can be stored; and a control step of instructing the compression unit to stop reading the captured image data when the compressed image data occupancy ratio is equal to or larger than the predetermined threshold value by a control unit, wherein the compression step further includes a step of generating the compressed image data according to a variable-length compression scheme in which fixed-length data is input and variable-length data is output, wherein the control step further includes a step of instructing the image capturing element to perform an image capturing operation, and when the captured image data which has not been read from the compression unit is present in the image capturing element, instructing the image capturing element not to perform the image capturing operation and instructing the image capturing element to perform the image capturing operation after the captured image data which has not been read from the compression unit is no longer present in the image capturing element, wherein the transmission buffering step further includes a step of storing the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount, of data that the compression unit reads at one time is capable of being stored, and wherein during the control step, when the compressed image data occupancy ratio is equal to or larger than the predetermined threshold value and the reading of the captured image data has not been completed for predetermined lines of the image capturing element, a step of delaying a timing of stopping reading of the captured image data until the reading of the captured image data is completed for the predetermined lines is performed by the control unit.

According to a ninth aspect of the present invention, there is provided a non-transitory medium saving a program for causing a computer to execute: an image capturing step of capturing images at a predetermined cycle and generating captured image data by an image capturing element; a compression step of dividedly reading one frame of the captured image data input from the image capturing element a plurality of times and performing a compression process on the captured image data to generate compressed image data by a compression unit; a transmitting step of wirelessly transmitting the compressed image data at a fixed bitrate by a transmitter; a transmission buffering step of receiving the compressed image data from the compression unit, storing the compressed image data, and outputting the compressed image data to the transmitter by a transmission buffer; a determining step of determining whether a compressed image data occupancy ratio is equal to or larger than a predetermined threshold value by a determining unit, the compressed image data occupancy ration indicating a ratio of an area in which the compressed image data is being stored to an area of the transmission buffer in which the compressed image data can be stored; and a control step of instructing the compression unit to stop reading the captured image data when the compressed image data occupancy ratio is equal to or larger than the predetermined threshold value by a control unit, wherein the compression step further includes a step of generating the compressed image data according to a variable-length compression scheme in which fixed-length data is input and variable-length data is output, wherein the control step further includes a step of instructing the image capturing element to perform an image capturing operation, and when the captured image data which has not been read from the compression unit is present in the image capturing element, instructing the image capturing element not to perform the image capturing operation and instructing the image capturing element to perform the image capturing operation after the captured image data which has not been read from the compression unit is no longer present in the image capturing element, wherein the transmission buffering step further includes a step of storing the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein during the control step, when the compressed image data occupancy ratio is equal to or larger than the predetermined threshold value and the reading of the captured image data has not been completed for predetermined lines of the image capturing element, a step of delaying a timing of stopping reading of the captured image data until the reading of the captured image data is completed for the predetermined lines is performed by the control unit.

DETAILED DESCRIPTION OF THE INVENTION

Embodiments of the present invention will be described with reference to the drawings.

First Embodiment

Figure 1:
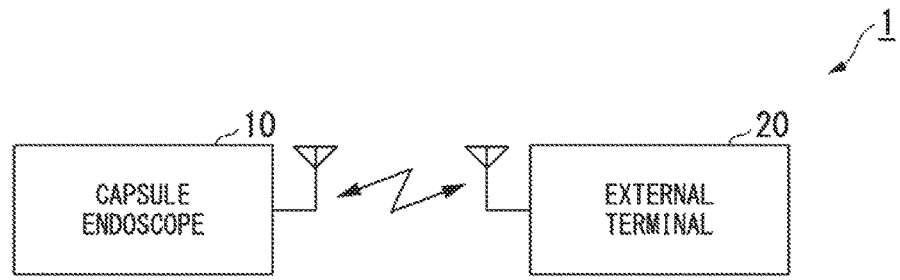
FIG. 1 is a schematic diagram showing a configuration of a capsule endoscope system according to a first embodiment of the present invention.

FIG. 1 is a schematic diagram showing a configuration of a capsule endoscope system 1 (a compressed image data transmitting and receiving system) according to a first embodiment of the present invention. In the example shown, the capsule endoscope system 1 includes a capsule endoscope 10 (a compressed image data transmitting device) and an external terminal 20 (a compressed image data receiving device).

The capsule endoscope 10 and the external terminal 20 can transmit and receive data by wireless communication. For example, the capsule endoscope 10 moves along the stomach, the small intestine, and the large intestine according to peristaltic movement thereof after the capsule endoscope 19 is swallowed through the mouth of a patient in order to perform observation of the inside of the body cavity. Moreover, for example, the capsule endoscope 10 captures an image of the inside of the body cavity when the capsule endoscope 10 is present inside the body cavity, and the capsule endoscope 10 transmits the captured image data to the external terminal 20 by wireless communication. The external terminal 20 stores the image data transmitted from the capsule endoscope 10. The image data stored in the external terminal 20 can be utilized for diagnosis or the like.

Figure 2:
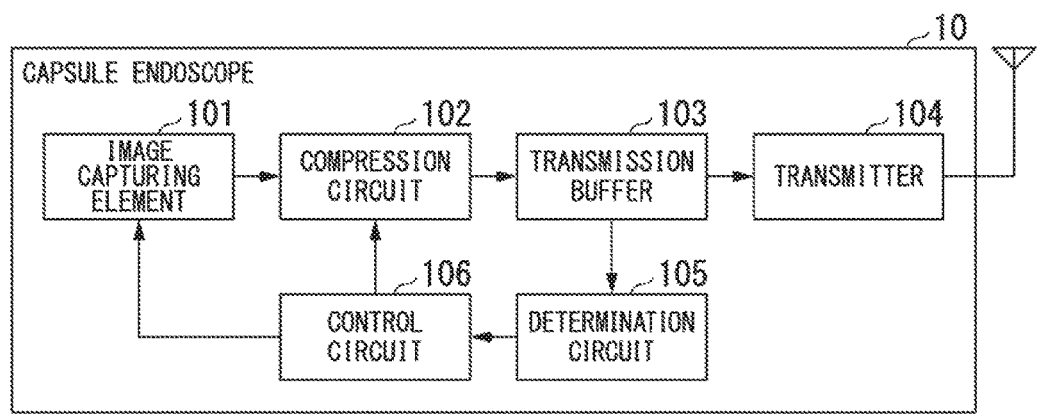
FIG. 2 is a block diagram showing a configuration of a capsule endoscope according to the first embodiment of the present invention.

FIG. 2 is a block diagram showing a configuration of the capsule endoscope 10 according to the present embodiment. In the example shown, the capsule endoscope 10 includes an image capturing element 101, a compression circuit 102, a transmission buffer 103, a transmitter 104, a determination circuit 105, and a control circuit 106.

The image capturing element 101 captures images at a designated frame rate (predetermined time intervals) according to the control of the control circuit 106 and the image capturing element 101 generate captured image data. The compression circuit 102 reads one frame of captured image data from the image capturing element 101 by several times. The compression circuit 102 generates compressed image data by compressing the image data read from the image capturing element 101 using predetermined parameters and the compression circuit 102 outputs the compressed image data to the transmission buffer 103.

The transmission buffer 103 receives the compressed image data from the compression circuit 102, the transmission buffer 103 stores the compressed image data, and the transmission buffer 103 outputs the compressed image data to the transmitter 104. The size (an area of the transmission buffer 103 in which the compressed image data can be stored) of the transmission buffer 103 is set to a size that is smaller than twice the amount of data that the compression circuit 102 can read as compressed image data at one time. The transmission buffer 103 has a structure (for example, a ring buffer or a two-sided buffer) such that compressed image data can be stored continuously. The transmission buffer 103 stores the input compressed image data until the input compressed image data is output to the transmitter 104 such that new compressed image data can be stored in a storage area in which the previous input compressed image data was stored when the previous input compressed image data has been output to the transmitter 104.

A compressed image data occupancy ratio is a value indicating the ratio of an area in which compressed image data is being stored to an area of the transmission buffer 103 in which the compressed image data can be stored.

The transmitter 104 including an antenna element acquires the compressed image data from the transmission buffer 103, the transmitter 104 modulates the acquired compressed image data, and the transmitter 104 wirelessly transmits the modulated compressed image data to the external terminal 20. In this case, the transmitter 104 is assumed to be a transmitter that is configured to wirelessly transmit the data at a fixed bit rate. The determination circuit 105 monitors the compressed image data occupancy ratio of the transmission buffer 103 and the determination circuit 105 determines whether the compressed image data occupancy ratio is equal to or larger than a threshold value. The determination circuit 105 outputs an occupancy ratio determination result to the control circuit 106. In this case, hysteresis may be introduced to the threshold value.

The control circuit 106 instructs the image capturing element 101 to perform an image capturing operation, while the control circuit 106 outputs a captured image readout instruction (an output continue instruction) and a captured image readout stop instruction (an output stop instruction) to the compression circuit 102 on the basis of the occupancy ratio determination result acquired from the determination circuit 105, wherein the captured image readout instruction is used for reading a captured image from the image capturing element 101, and the captured image readout stop instruction is used for stopping reading of the captured image. The control circuit 106 instructs the image capturing element 101 to perform an image capturing operation, and in a situation in which the captured image data which has not been read from the compression circuit 102 is present in the image capturing element 101, the control circuit 106 instructs the image capturing element 101 not to perform an image capturing operation, while the control circuit 106 instructs the image capturing element 101 to perform an image capturing operation after captured image data which has not been read from the compression circuit 102 is no longer present in the image capturing element 101.

Figure 3:
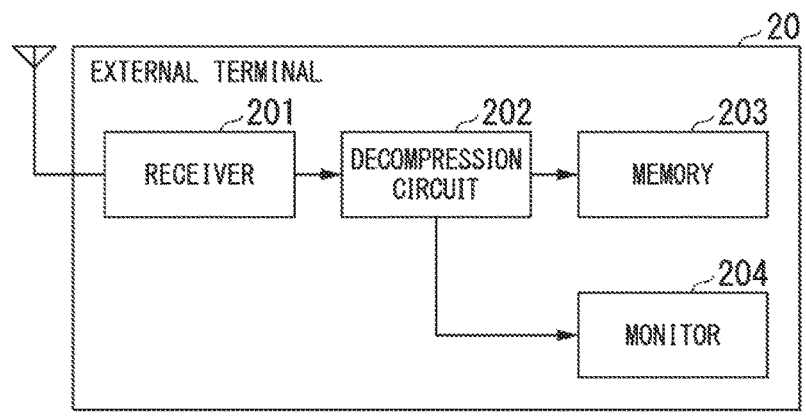
FIG. 3 is a block diagram showing a configuration of an external terminal according to the first embodiment of the present invention.

FIG. 3 is a block diagram showing a configuration of the external terminal 20 according to the present embodiment. In the example shown, the external terminal 20 includes a receiver 201, a decompression circuit 202, a memory 203, and a monitor 204.

The receiver 201 includes an antenna element, the receiver 201 receives signals transmitted from the capsule endoscope 10, the receiver 201 demodulates compressed image data, and the receiver 201 outputs the modulated, compressed image data to the decompression circuit 202. The decompression circuit 202 decompresses the compressed image data acquired from the receiver 201 using predetermined parameters to generate image data, and the decompression circuit 202 outputs the image data to the memory 203 and the monitor 204.

The memory 203 stores the image data acquired from the decompression circuit 202. The monitor 204 displays the image data acquired from the decompression circuit 202.

Figure 4:
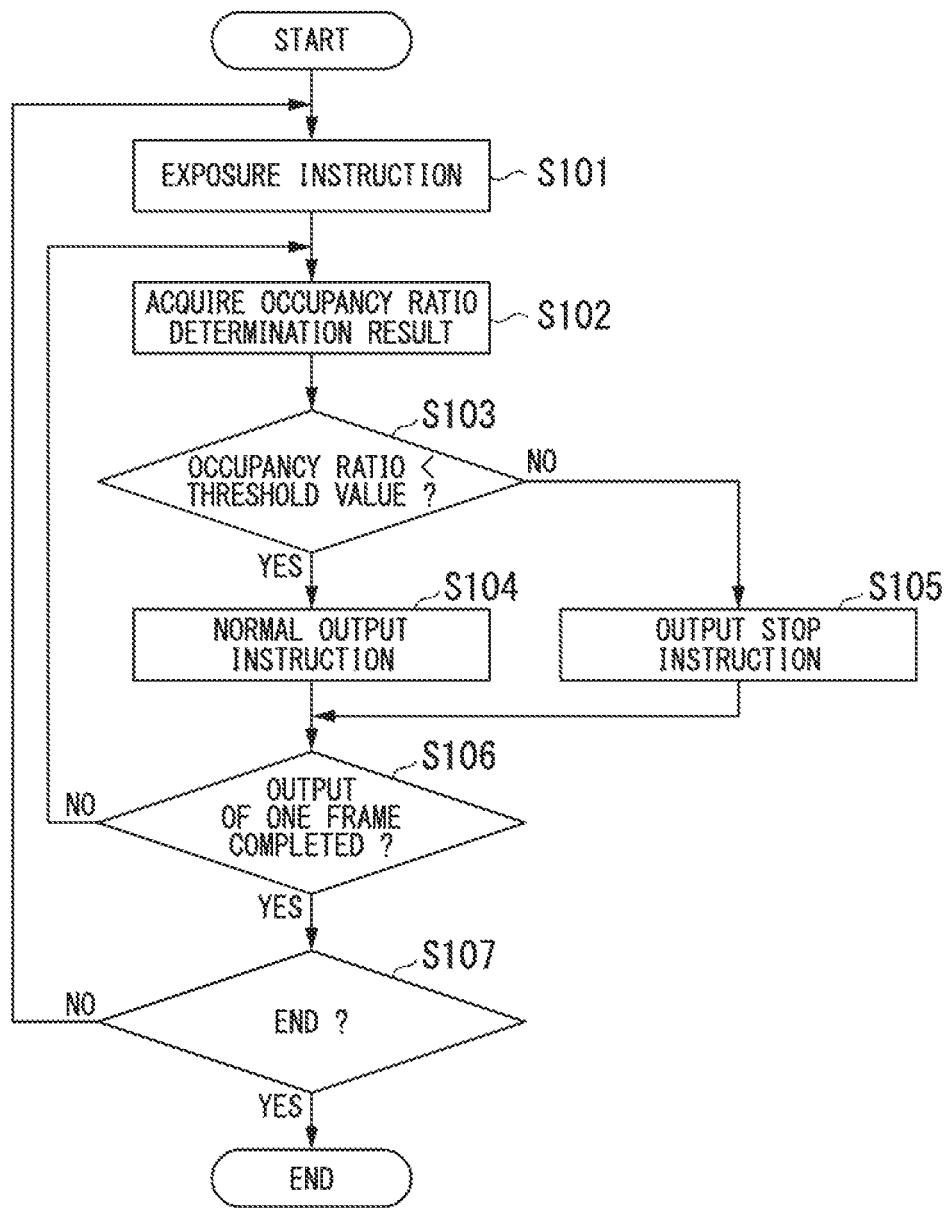
FIG. 4 is a flowchart showing the flow of processing of a control circuit of the capsule endoscope according to the first embodiment of the present invention.

Next, the flow of processing of the control circuit 106 of the capsule endoscope 10 according to the present embodiment will be described. FIG. 4 is a flowchart showing the flow of processing of the control circuit 106 of the capsule endoscope 10 according to the present embodiment.

(Step S101)

The control circuit 106 outputs an exposure instruction to the image capturing element 101, and the control circuit 106 sequentially waits only for a predetermined exposure period such that one frame of image data is generated. After that, the flow proceeds to step S102. The process of step S101 is referred to as an exposure instruction step.

(Step S102)

The control circuit 106 acquires an occupancy ratio determination result from the determination circuit 105. After that, the flow proceeds to step S103. The process of step S102 is referred to as an occupancy ratio acquisition step.

(Step S103)

The control circuit 106 performs the process of step S104 when the occupancy ratio determination result is smaller than a predetermined threshold value, and the control circuit 106 performs the process of step S105 when the occupancy ratio determination result is equal to or larger than the predetermined threshold value. The process of step S103 is referred to as a determination result judgment step.

(Step S104)

The control circuit 106 outputs an output, continue instruction to the compression circuit 102 and the control circuit 106 performs the process of step S106. When an output continue instruction is input, the compression circuit 102 reads image data from the image capturing element 101, the compression circuit 102 generates compressed image data, and the compression circuit 102 outputs the compressed image data to the transmission buffer. The process of step S104 is referred to as an output, continue instruction step.

(Step S105)

The control circuit 106 outputs an output stop instruction to the compression circuit 102 and the control circuit 106 performs the process of step S106. When an output stop instruction is input, the compression circuit 102 stops the process of reading image data from the image capturing element 101. The process of step S105 is referred to as an output stop instruction step.

(Step S106)

The control circuit 106 determines whether one frame of image data generated in step S101 by the image capturing element 101 has been completely output. When it is determined that one frame of image data generated in step S101 has been completely output, the flow proceeds to step S107. When it is determined that one frame of image data generated in step S101 has not been completely output, the flow proceeds to step S102. The process of step S106 is referred to as a frame completion determination step.

(Step S107)

The control circuit 106 performs end determination which is determination of whether the operation of the capsule 10 has ended. As the end determination of the capsule endoscope 10, it is determined that the operation of the capsule endoscope 10 has ended when a decrease in voltage of a battery (not shown) is detected, for example. The process ends when it is determined that the operation of the capsule endoscope 10 has ended. Moreover, the flow returns to step S101 when it is determined that the operation of the capsule endoscope 10 has not ended. The process of step S107 is referred to as a frame completion determination process.

Next, the relation between an occupancy ratio determination result output by the determination circuit 105, the operation of the control circuit 106, and the operation of the image capturing element 101 according to the present embodiment will be described with reference to FIGS. 5 to 7.

First, a case in which the compressed image data stored in the transmission buffer 103 does not exceed a predetermined threshold value among the storage areas of the transmission buffer 103 will be described. FIG. 5 is a timing chart showing timings at which the control circuit 106 outputs an exposure instruction to the image capturing element 101, timings at which the compression circuit 102 reads image data from the image capturing element 101, and timings at which the determination result of the determination circuit 105 is output.

In the example shown, the determination circuit 105 outputs a signal (a signal LOW in the example shown) indicating that the occupancy ratio determination result is smaller than a predetermined threshold value. That is, in the example shown, the compressed image data stored in the transmission buffer 103 does not exceed a predetermined threshold value among the storage areas of the transmission buffer 103.

In the example shown, in a period between time point t1 and time point t2, the control circuit 106 instructs the image capturing element 101 to perform one frame of exposure (step S101 in FIG. 4). After exposure ends at time point t2, the control circuit 106 acquires an occupancy ratio determination result from the determination circuit 105 (step S102 in FIG. 4). Moreover, when it is determined that the occupancy ratio determination result is smaller than the predetermined threshold value (step S103: Y in FIG. 4), the control circuit 106 outputs an output continue instruction to the compression circuit 102 (step S104 in FIG. 4). The compression circuit 102 reads image data sequentially from the image capturing element 101 on the basis of the output continue instruction.

The control circuit 106 repeatedly performs the process shown in FIG. 4. Specifically, in the example shown in FIG. 5, the control circuit 106 acquires the occupancy ratio determination result from the determination circuit 105 and determines whether the occupancy ratio determination, result is smaller than the predetermined threshold value. The control circuit 106 outputs the output continue instruction to the compression circuit 102 when the occupancy ratio determination result is smaller than the predetermined threshold value, and the control circuit 106 outputs the output stop instruction to the compression circuit 102 when the occupancy ratio determination result is equal to or larger than the predetermined threshold value (steps S102 to S105 in FIG. 4). Moreover, the control circuit 106 determines whether the compression circuit 102 has completely read one frame of image data generated by the image capturing element 101 in step S101. The control circuit 106 performs the process of step S102 when it is determined that reading of one frame of image data has not been completed (step S106 in FIG. 4).

Accordingly, in the period between time point t2 and time point t3, the compression circuit 102 reads image data sequentially on the basis of the output continue instruction. When it is determined that output of one frame of image data is completed at time point t3, the control circuit 106 returns to the process of step S101 and the control circuit 106 instructs the image capturing element 101 to perform exposure of one frame of image data in a period between time point t3 and time point t4 (step S101 in FIG. 4). The processes subsequent to time point t4 are the same as the processes subsequent to time point t2.

Figure 6:
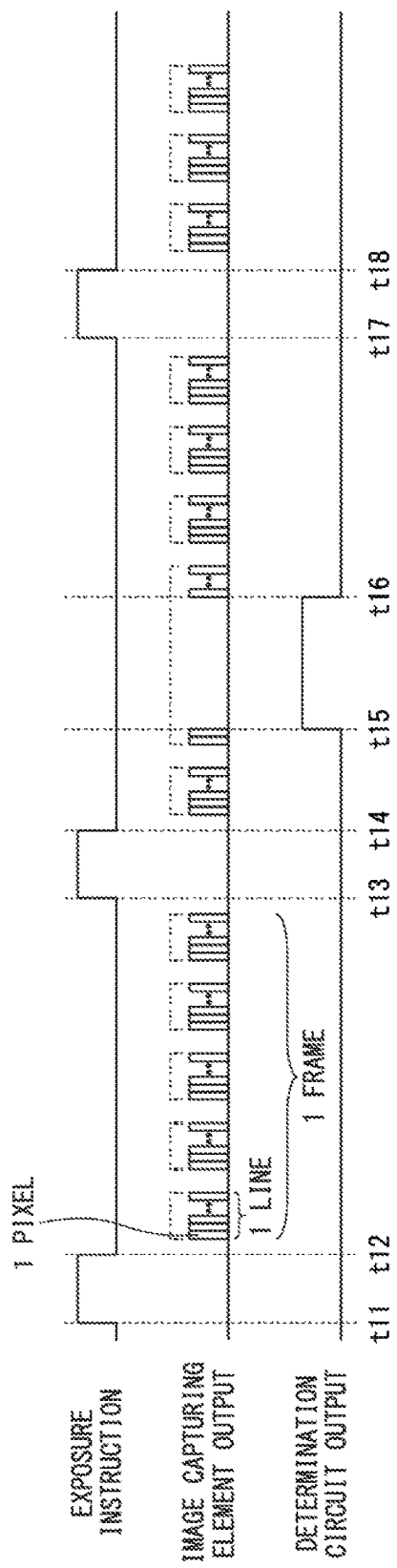
FIG. 6 is a timing chart showing timings at which the control circuit issues an exposure instruction to an image capturing element, timings at which the image capturing element outputs image data, and timings at which a determination circuit outputs a determination result according to the first embodiment of the present invention.
Figure 7:
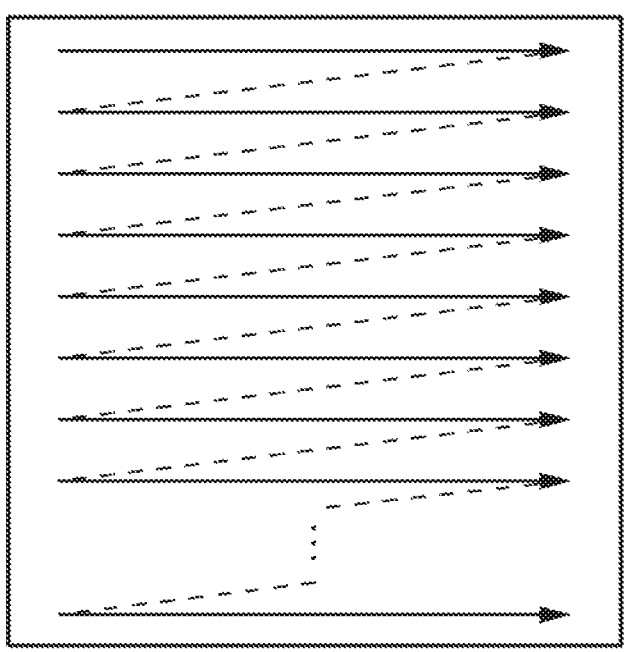
FIG. 7 is a schematic diagram showing the order in which the image capturing element outputs image data according to the first embodiment of the present invention.

In this case, reading of image data is performed sequentially for each line from a top-left corner to a bottom-right corner of a pixel arrangement of the image capturing element 101 as shown in FIG. 7, for example. FIG. 7 is a schematic diagram showing the order in which the compression circuit 102 reads image data. In the example shown in FIGS. 5 to 7, it is described that the compression circuit 102 reads image data sequentially for each line from the top-left corner to the bottom-right corner of the pixel arrangement of the image capturing element 101 and a blank period is provided between lines, however, the present invention is not limited to this. For example, image data may not be read successively and the blank period may not be provided, and other readout methods may be used. Furthermore, rather than reading image data successively, a valid pixel region of the image capturing element 101 may be determined in advance depending on the specification of the image capturing element 101 and the image data in the region may be read.

Subsequently, a case in which the compressed image data stored in the transmission buffer 103 exceeds the predetermined threshold value among the storage areas of the transmission buffer 103 will be described. FIG. 6 is a timing chart showing timings at which the control circuit 106 outputs an exposure instruction to the image capturing element 101, timings at which the compression circuit 102 reads image data from the image capturing element 101, and timings at which the determination result of the determination circuit 105 is output.

In the example shown, in a period other than the period between time point t15 and time point t16, the determination circuit 105 outputs a signal (a signal LOW in the example shown) indicating that the occupancy ratio determination result is smaller than a predetermined threshold value. Moreover, in the period between time point t15 and time point t16, the determination circuit 105 outputs a signal (a signal HI in the example shown) indicating that the occupancy ratio determination result is equal to or larger than the predetermined threshold value.

That is, in the example shown, in a period other than the period between time point t15 and time point t16, the compressed image data stored in the transmission buffer 103 does not exceed the predetermined threshold value among the storage areas of the transmission buffer 103. Moreover, in the period between time point t15 and time point t16, the compressed image data stored in the transmission buffer 103 exceeds the predetermined threshold value among the storage areas of the transmission buffer 103.

Figure 5:
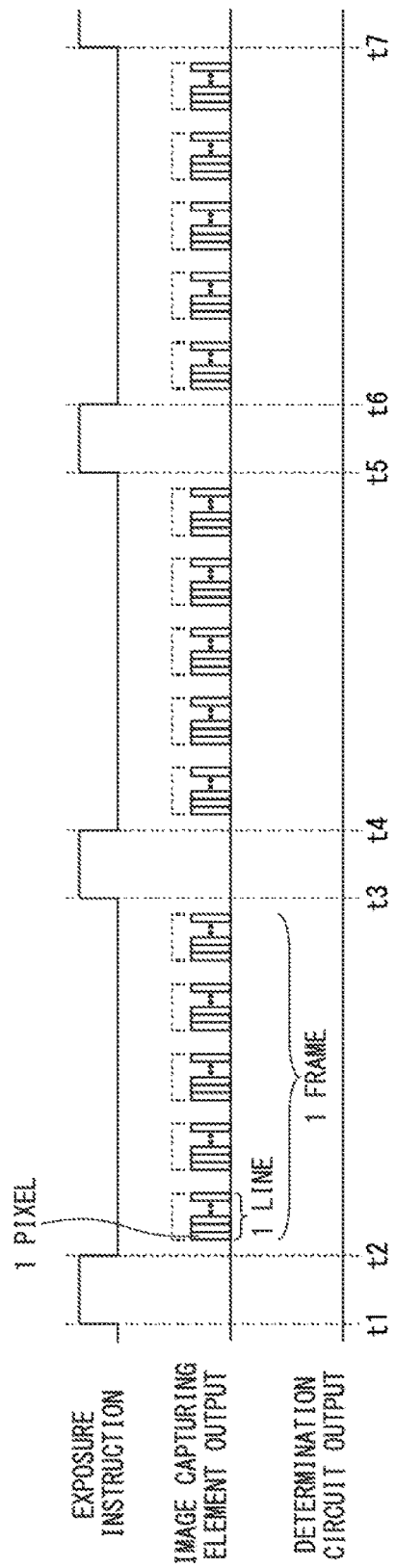
FIG. 5 is a timing chart showing timings at which the control circuit issues an exposure instruction to an image capturing element, timings at which the image capturing element outputs image data, and timings at which a determination circuit outputs a determination result according to the first embodiment of the present invention.

In the example shown, the operation in the period between time point t11 and time point t13 is the same as that of the example shown in FIG. 5. Moreover, in the example shown, in the period between time point t13 and time point t14, the control circuit 106 instructs the image capturing element 101 to perform exposure of one frame of image data (step S101 in FIG. 4). After exposure ends at time point t14, the control circuit 106 acquires an occupancy ratio determination result from the determination circuit 105 (step S102 in FIG. 4). When it is determined that the occupancy ratio determination result is smaller than the predetermined threshold value (step S103: Y in FIG. 4), the control circuit 106 outputs an output continue instruction to the compression circuit 102 (step S104 in FIG. 4). The compression circuit 102 reads image data sequentially from the image capturing element 101 on the basis of the output continue instruction.

The control circuit 106 repeatedly performs the process shown in FIG. 4. Specifically, in the example shown in FIG. 6, the control circuit 106 acquires an occupancy ratio determination result from the determination circuit 105 and the control circuit 106 determines whether the occupancy ratio determination result is smaller than the predetermined threshold value. The control circuit 106 outputs an output continue instruction to the compression circuit 102 when the occupancy ratio determination result is smaller than the predetermined threshold value, and the control circuit 106 outputs an output stop instruction to the compression circuit 102 when the occupancy ratio determination result is equal to or larger than the predetermined threshold value (steps S102 to S105 in FIG. 4). In the present embodiment, when the occupancy ratio determination result is smaller than the threshold value at time point t16, the control circuit 106 immediately outputs an output continue instruction to the compression circuit 102 such that reading of the image data is restarted.

In the example shown in FIG. 6, in the period between time point, t14 and time point t15 and the period between time point t16 and time point t17, the compression circuit 102 reads image data sequentially from the image capturing element 101 on the basis of the output continue instruction. Moreover, in the period between time point t15 and time point t16, the compression circuit 102 stops reading the image data on the basis of the output stop instruction.

The control circuit 106 determines whether the compression circuit 102 has completely read one frame of image data generated by the image capturing element 101 in step S101. When it is determined that reading of one frame of image data has not been completed, the flow returns to the process of step S102 (step S106 in FIG. 4). When it is determined that reading of one frame of image data has been completed at time point t17, the control circuit 106 returns to the process of step S101 and instructs the image capturing element 101 to perform exposure of one frame of image data in the period between time point t17 and time point t18 (step S101 in FIG. 4). The subsequent processes are the same as the above-described processes.

As described above, according to the present embodiment, the image capturing element 101 captures images at a predetermined cycle and the image capturing element 101 generates the captured image data. The compression circuit 102 dividedly reads one frame of captured image data from the image capturing element 101 a plurality of times, and the compression circuit 102 performs a compression process on the captured image data to generate compressed image data. The transmitter 104 wirelessly transmits the compressed image data at a fixed bitrate. The transmission buffer 103 receives the compressed image data from the compression circuit 102, the transmission buffer 103 stores the compressed image data, and the transmission buffer 103 outputs the compressed image data to the transmitter 104.

The determination circuit 105 determines whether a compressed image data occupancy ratio is equal to or larger than the predetermined threshold value, the compressed image data occupancy ratio indicating the ratio of an area in which the compressed image data is stored to an area in which the compressed image data of the transmission buffer can be stored. Furthermore, the control circuit 106 instructs the compression circuit 102 to stop reading the captured image data when the compressed image data occupancy ratio is equal to or larger than the predetermined threshold value.

The compress ion circuit 102 gene rates compressed image data according to a variable-length compression scheme that is configured to receive fixed-length data and outputs variable-length data. The control circuit 106 instructs the image capturing element 101 to perform an image capturing operation, and when the captured image data which has not been read from the compression circuit 102 is present in the image capturing element 101, the control circuit 106 firstly instructs the image capturing element 101 not to perform an image capturing operation, and the control circuit 106 subsequently instructs the image capturing element 101 to perform the image capturing operation after the captured image data which has not been read from the compression circuit 102 is no longer present in the image capturing element 101.

The transmission buffer 103 stores the compressed image data until the input compressed image data is output to the transmitter 104 such that when the compressed image data is output to the transmitter 104, new compressed image data can be stored in a storage area in which the compressed image data was stored. An area of the transmission buffer 103 in which the compressed image data can be stored is an area in which an amount of data that is smaller than twice the amount of data that the compression circuit 102 can read as captured image data at one time can be stored.

Due to such a configuration, when the compressed image data occupancy ratio of the transmission buffer 103 is high, the image capturing element 101 stops outputting the image data on the basis of an output stop instruction. As a result, the situation that there is insufficient storage capacity in the transmission buffer 103 is prevented. Accordingly, it is not necessary to increase the image compression rate even when the compressed image data occupancy ratio of the transmission buffer is high, and it is possible to transmit the compressed image data reliably while preventing a deterioration of image quality due to an increase in the image compression rate.

Figure 8:
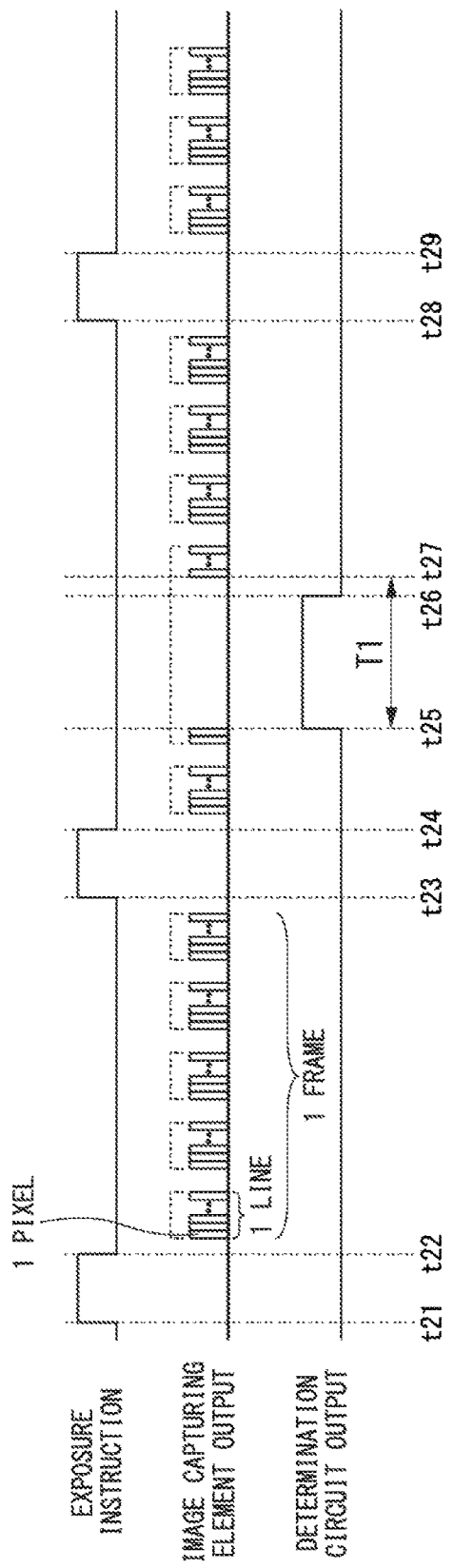
FIG. 8 is a timing chart showing timings at which the control circuit issues an exposure instruction to an image capturing element, timings at which the image capturing element outputs image data, and timings at which a determination circuit outputs a determination result according to the first embodiment of the present invention.

Next, a modification example of the first embodiment will be described. FIG. 8 is a timing chart showing timings at which the control circuit 106 of this modification example outputs an exposure instruction to the image capturing element 101, timings at which the image capturing element 101 outputs image data, and timings at which the determination result of the determination circuit 105 is output. A description of components the same as those of the first embodiment will be omitted.

The timings at which the control circuit 106 instructs the compression circuit 102 to restart reading the image data in the modification example are different from those of the first embodiment. In this modification example, when the compressed image data occupancy ratio of the transmission buffer 103 is equal to or larger than the threshold value at time point t25 in which image data is being output, and the occupancy ratio determination result output by the determination circuit 105 changes from a signal indicating that the occupancy ratio determination result is smaller than the predetermined threshold value to a signal indicating that the occupancy ratio determination result is equal to or larger than the predetermined threshold value (the signal LOW changes to the signal HI in the example shown), the control circuit 106 instructs the compression circuit 102 to stop outputting the image data in a predetermined period T1. At time point t27 after the predetermined period T1 has elapsed, the control circuit 106 instructs the compression circuit 102 to restart reading the image data.

As described above, in the modification example, when the compressed image data occupancy ratio of the transmission buffer 103 is high, the compression circuit 102 stops reading the image data on the basis of an output stop instruction. Accordingly, the situation that there is insufficient storage capacity in the transmission buffer 103 is prevented. Accordingly, it is not necessary to increase the image compression rate even when the compressed image data occupancy ratio of the transmission buffer is high, and it is possible to transmit the compressed image data reliably while preventing a deterioration of image quality due to an increase in the image compression rate.

Second Embodiment

Next, a second embodiment of the present invention will be described. The present embodiment is different from the first embodiment in that reading from the image capturing element 101 is controlled for each of predetermined lines. The configuration including the capsule endoscope 10 and the external terminal 20 is the same as that of the first embodiment.

Hereinafter, the flow of the processing of the control circuit 106 of the capsule endoscope 10 according to the present embodiment will be described. FIG. 3 is a flowchart showing the flow of the processing of the control circuit 106 of the capsule endoscope 10 according to the present embodiment.

The processes of steps S201 to S204 are the same as the processes of steps S101 to S104 of the first embodiment.
(Step S205)

The control circuit 106 determines whether reading of image data has been completed up to a predetermined line in which image data is currently being read. When it is determined that reading of image data has been completed up to a predetermined line in which image data is currently being read, the flow proceeds to the process of step S206. When it is determined that reading of image data has not been completed up to a predetermined line in which image data is currently being read, the process of step S205 is executed again. The process of step S205 is referred to as a predetermined line output determination step.

The processes of steps S206 to S208 are the same as the processes of steps S105 to S107 of the first embodiment.

Next, the relation between the occupancy ratio determination result output by the determination circuit 105, the operation of the control circuit 106, and the operation of the image capturing element 101 according to the present embodiment will be described with reference to FIG. 10.

Figure 10:
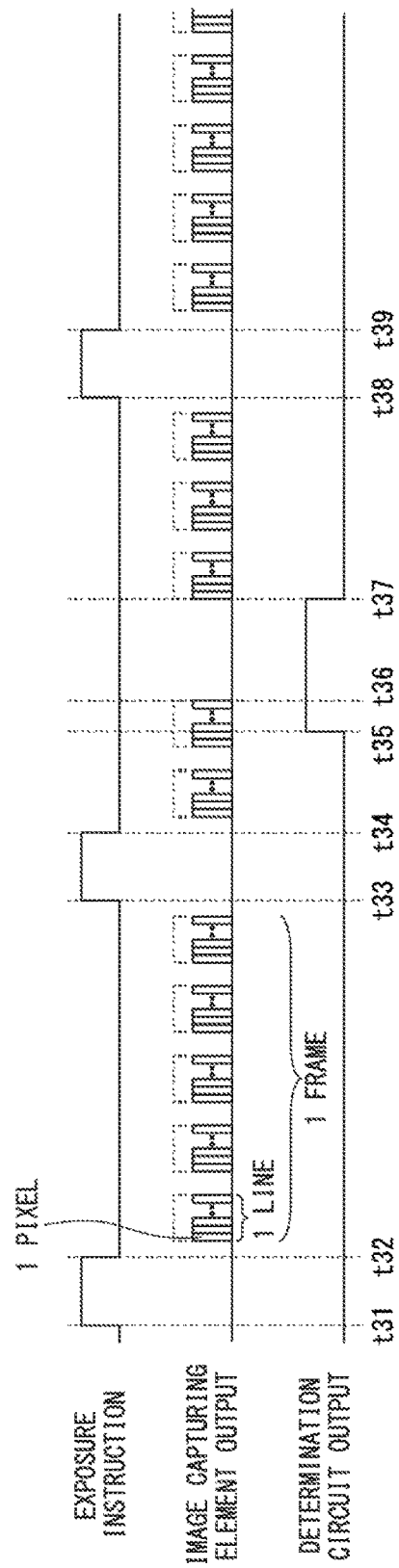
FIG. 10 is a timing chart showing timings at which the control circuit issues an exposure instruction to an image capturing element, timings at which the image capturing element outputs image data, and timings at which a determination circuit outputs a determination result according to the second embodiment of the present invention.

FIG. 10 is a timing chart showing timings at which the control circuit 106 outputs an exposure instruction to the image capturing element 101, timings at which the compression circuit 102 reads image data, and timings at which the determination result of the determination circuit 105 is output.

In the example shown, in a period other than the period between time point t35 and time point t37, the determination circuit 105 outputs a signal (a signal LOW in the example shown) indicating that the occupancy ratio determination result, is smaller than a predetermined threshold value. In the period between time point t35 and time point t37, the determination circuit 105 outputs a signal (a signal HI in the example shown) indicating that, the occupancy ratio determination result is equal to or larger than the predetermined threshold value.

That is, in the example shown in a period other than the period between time point t35 and time point t37, the compressed image data stored in the transmission buffer 103 does not exceed a predetermined threshold value among the storage areas of the transmission buffer 103. In the period between time point t35 and time point t37, the compressed image data stored in the transmission buffer 103 exceeds the predetermined threshold value among the storage areas of the transmission buffer 103.

Figure 9:
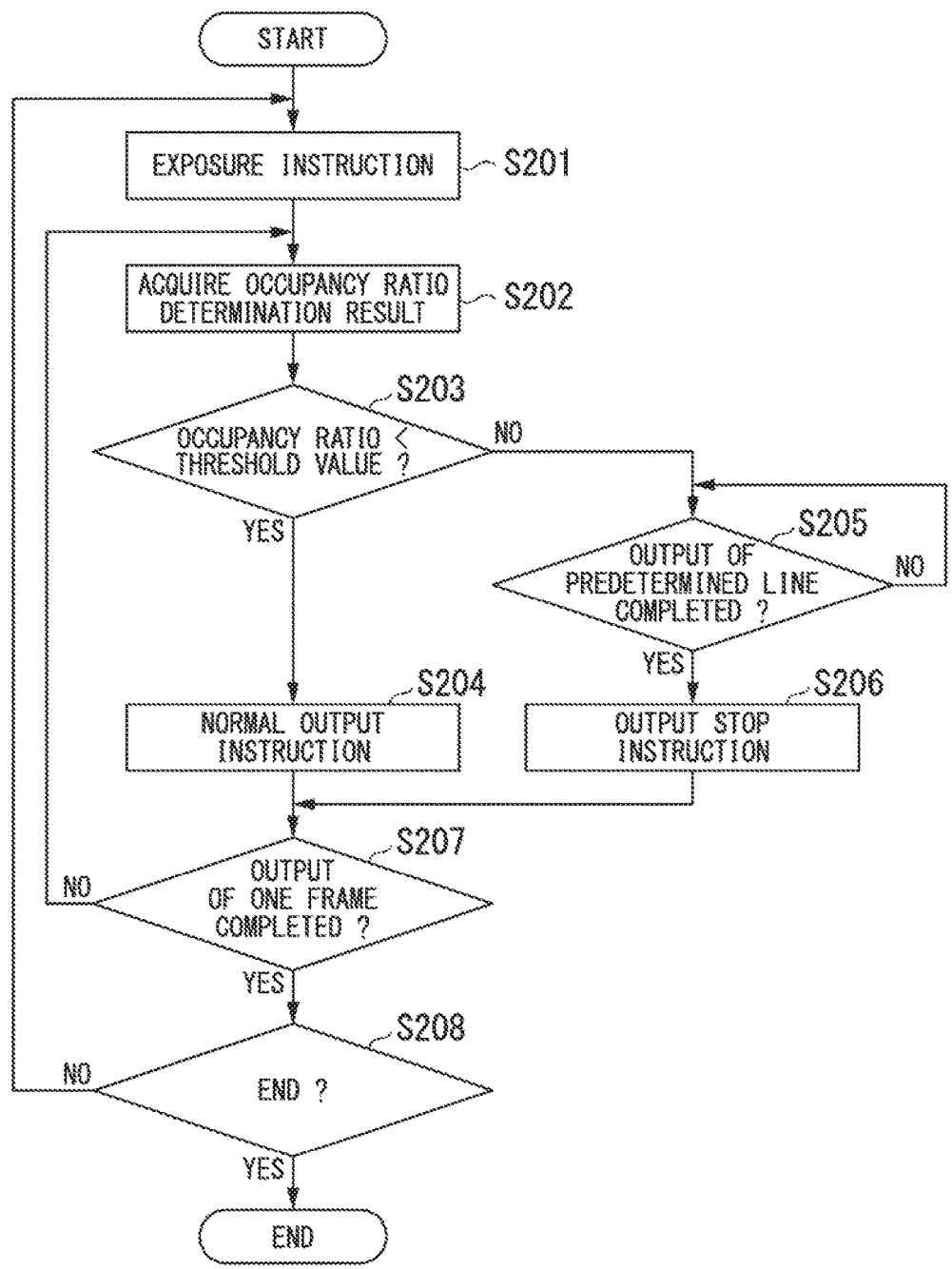
FIG. 9 is a flowchart showing the flow of processing of a control circuit of a capsule endoscope according to a second embodiment of the present invention.

In the example shown, the operation in the period between time point t31 and time point t33 is the same as that of the example shown in FIG. 5 in the first embodiment. In the example shown, in the period between time point t33 and time point t34, the control circuit 106 instructs the image capturing element 101 to perform exposure of one frame, of image data (step S201 in FIG. 9). After exposure ends at time point t34, the control circuit 106 acquires an occupancy ratio determination result from the determination circuit 105 (step S202 in FIG. 9). When it is determined that the occupancy ratio determination result is smaller than the predetermined threshold value (step S203: Y in FIG. 9), the control circuit 106 outputs an output continue instruction to the compression circuit 102 (step S204 in FIG. 9). The compression circuit 102 reads image data sequentially from the image capturing element 101 on the basis of the output continue instruction.

The control circuit 106 repeatedly performs the process shown in FIG. 3. Specifically, in the example shown in FIG. 10, the control circuit 106 acquires an occupancy ratio determination result from the determination circuit 105 and the control circuit 106 determines whether the occupancy ratio determination result is smaller than the predetermined threshold value. The control circuit 106 outputs an output continue instruction to the compression circuit 102 when the occupancy ratio determination result is smaller than the predetermined threshold value (steps S204 in FIG. 9).

When the occupancy ratio determination result is equal to or larger than the predetermined threshold value, the control circuit 106 determines whether reading of the image data has been completed up to a predetermined line in which image data is currently being read. When it is determined that reading of the image data has not been completed up to a predetermined line in which image data is currently being read, the process of step S205 is executed again. When it is determined that reading of the image data has been completed up to a predetermined line in which image data is currently being read, the control circuit 106 outputs an output stop instruction to the compression circuit 102 (steps S205 to S206 in FIG. 9). In the present embodiment, when the occupancy ratio determination result is smaller than the threshold value at time point t37, the control circuit 106 immediately outputs an output continue instruction to the compression circuit 102 such that reading of the image data is restarted.

In the example shown in FIG. 10, in the period between time point t34 and time point t36 and the period between time point t37 and time point t38, the compression circuit 102 outputs image data sequentially from the image capturing element 101 on the basis of the output continue instruction. In the period between time point t36 and time point t37, the compression circuit 102 stops reading the image data on the basis of the output stop instruction.

The control circuit 106 determines whether the compression circuit 102 has completely read one frame of image data generated by the image capturing element 101 in step S201. When it is determined that reading of one frame of image data has been completed, the flow returns to the process of step S202 (step S207 in FIG. 9). When it is determined that reading of one frame of image data has been completed at time point t38, the control circuit 106 returns to the process of step S201 and the control circuit 106 instructs the image capturing element 101 to perform exposure of one frame of image data in the period between time point t38 and time point t39 (step S201 in FIG. 9). The subsequent processes are the same as the above-described processes.

As described above, according to the present embodiment, when the compressed image data occupancy ratio of the transmission buffer 103 is high, the compression circuit 102 stops reading the image data on the basis of an output stop instruction after outputting of image data for a predetermined line is completed. In this way, a situation that there is insufficient storage capacity in the transmission buffer 103 is prevented. Moreover, according to the present embodiment, the compression circuit 102 performs reading of image data and stopping reading for a predetermined line. Accordingly, the compression circuit 102 can perform processing for respective predetermined lines, and it is possible to simplify the configuration of the compression circuit 102.

Accordingly, it is not necessary to increase the image compression rate even when the compressed image data occupancy ratio of the transmission buffer is high while the configuration of the compression circuit 102 is simplified, such that it is possible to transmit the compressed image data reliably while preventing a deterioration of image quality due to an increase in the image compression rate.

In the above-described example, although predetermined lines are one line, the present invention is not limited to this. For example, a predetermined number of lines may be a plurality of lines. The predetermined number of lines may be determined according to the operation of the compression circuit 102. For example, when a compression circuit 102 that performs compression in four lines is used, the predetermined number of lines may be set to four lines.

Figure 11:
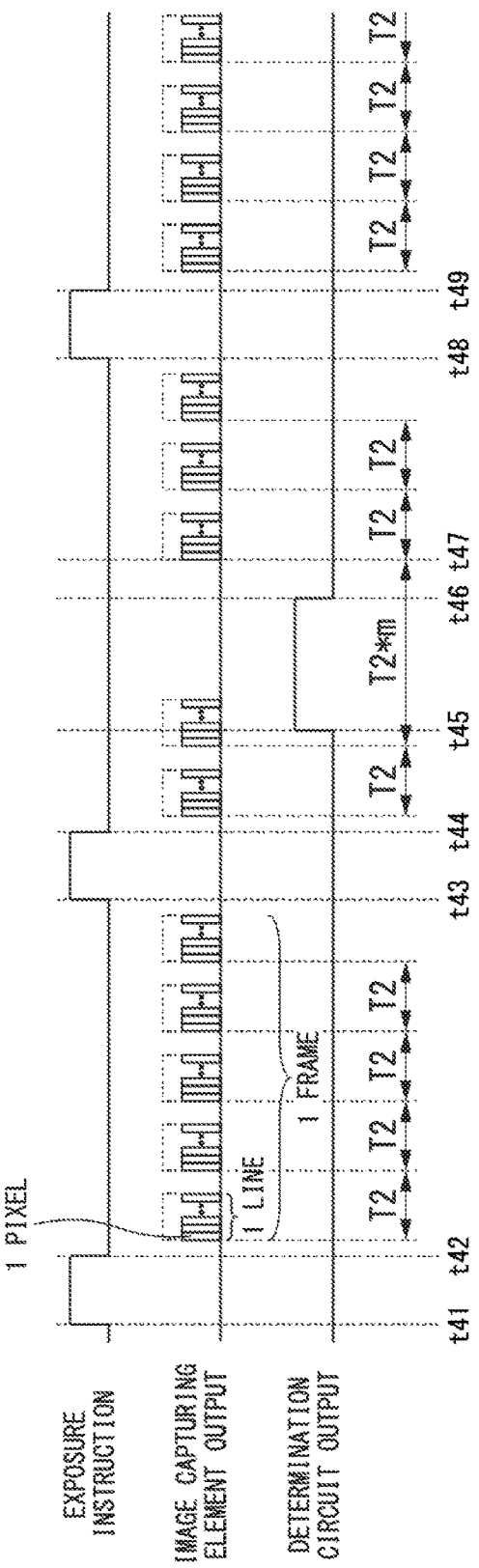
FIG. 11 is a timing chart for describing an operation of an image capturing element when an output stop instruction is issued according to a modification example of the second embodiment of the present invention.

Next, a modification example of the second embodiment will be described. FIG. 11 is a timing chart for describing the operation of the image capturing element 101 when an output stop instruction is issued according to this modification example. A description of components the same as those of the second embodiment will fee omitted. This modification example and the second embodiment are different in that the timing at which the control circuit 106 instructs the compression circuit 102 to restart reading image data is an integer multiple of a prescribed time period later than the timing at which reading of image data started before reading of image data stopped.

In the modification example, when the control circuit 106 instructs the compression circuit 102 to read image data, the control circuit 106 instructs the compression circuit 102 to read image data at prescribed time periods (T2) for each line. After that, when the compressed image data occupancy ratio of the transmission buffer 103 is equal to or larger than the threshold value at time point t45 in which image data is being read, and the occupancy ratio determination result output by the determination circuit 105 changes from a signal indicating that the occupancy ratio determination result is smaller than the predetermined threshold value to a signal indicating that the occupancy ratio determination result is equal to or larger than the predetermined threshold value (the signal LOW changes to the signal HI in the example shown), the control circuit 106 instructs the compression circuit 102 to continue reading a predetermined line of image data and then instructs the compression circuit 102 to stop outputting the image data.

After the occupancy ratio determination result output by the determination circuit 105 changes from a signal indicating that the occupancy ratio determination result is equal to or larger than the predetermined threshold value to a signal indicating that the occupancy ratio determination result is smaller than the predetermined threshold value (the signal HI changes to the signal LOW in the example shown), the control circuit 106 instructs the compression circuit 102 to restart reading image data at a timing (time point t47 in FIG.

11) which is TH=T2*m (m is an arbitrary natural number) later than the timing at which reading of image data started before reading of image data stopped.

As described above, according to the modification example, the control circuit 106 instructs the compression circuit 102 to read image data at a prescribed cycle (T2) for each line. The control circuit 106 instructs the compression circuit 102 to restart reading the image data at a timing which is an integer multiple of a prescribed cycle later than the timing at which reading of image data started before outputting of image data was stopped. Accordingly, since the compression circuit 102 can perform the compression process in respective predetermined lines at predetermined intervals, the configuration of the compression circuit 102 can be simplified.

Even the configuration of the compression circuit 102 is simplified, when the compressed image data occupancy ratio of the transmission buffer 103 is high, the compression circuit 102 stops reading the image data on the basis of an output stop instruction. Accordingly, a situation that there is insufficient storage capacity in the transmission buffer 103 is prevented. Accordingly, it is not necessary to increase the image compression rate even when the compressed image data occupancy ratio of the transmission buffer is high such that it is possible to transmit the compressed image data reliably while preventing a deterioration of image quality due to an increase in the image compression rate.

Third Embodiment

Next, a third embodiment of the present invention will be described. The present embodiment is different from the modification example of the second embodiment in that the control circuit 106 controls the timings of issuing an exposure instruction to the image capturing element 101 at a predetermined cycle. The configuration including the capsule endoscope 10 and the external terminal 20 is the same as the configuration thereof in the modification example of the second embodiment.

Figure 12:
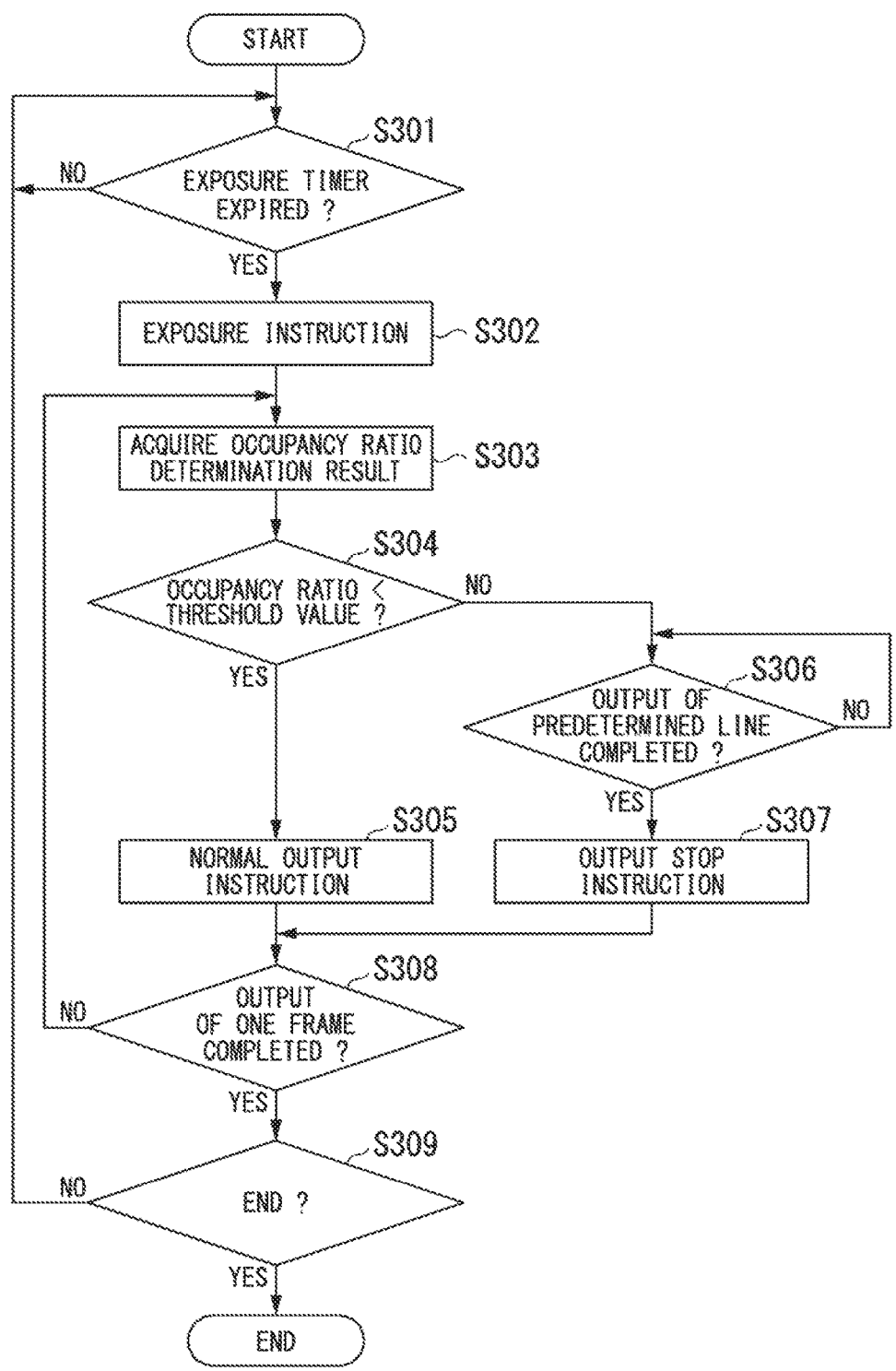
FIG. 12 is a flowchart showing the flow of processing of a control circuit of a capsule endoscope according to a third embodiment of the present invention.

Hereinafter, the flow of the processing of the control circuit 106 of the capsule endoscope 10 according to the present embodiment will be described. FIG. 12 is a flowchart showing the flow of the processing of the control circuit 106 of the capsule endoscope 10 according to the present embodiment.
(Step S301)

The control circuit 106 sets a timer (not shown) to a predetermined time period TE and waits until the timer reaches TE=T3*n (n is an arbitrary natural number). At the timing of TE, the flow proceeds to step S302. The process of step S301 is referred to as an exposure timer expiration determination step.

The processes of steps S302 to S309 are the same as the processes of steps S201 to S208 of the second embodiment.

Next, the relation between the occupancy ratio determination result output by the determination circuit 105, the operation of the control circuit 106, and the operation of the image capturing element 101 according to the present embodiment will be described with reference to FIG. 13.

Figure 13:
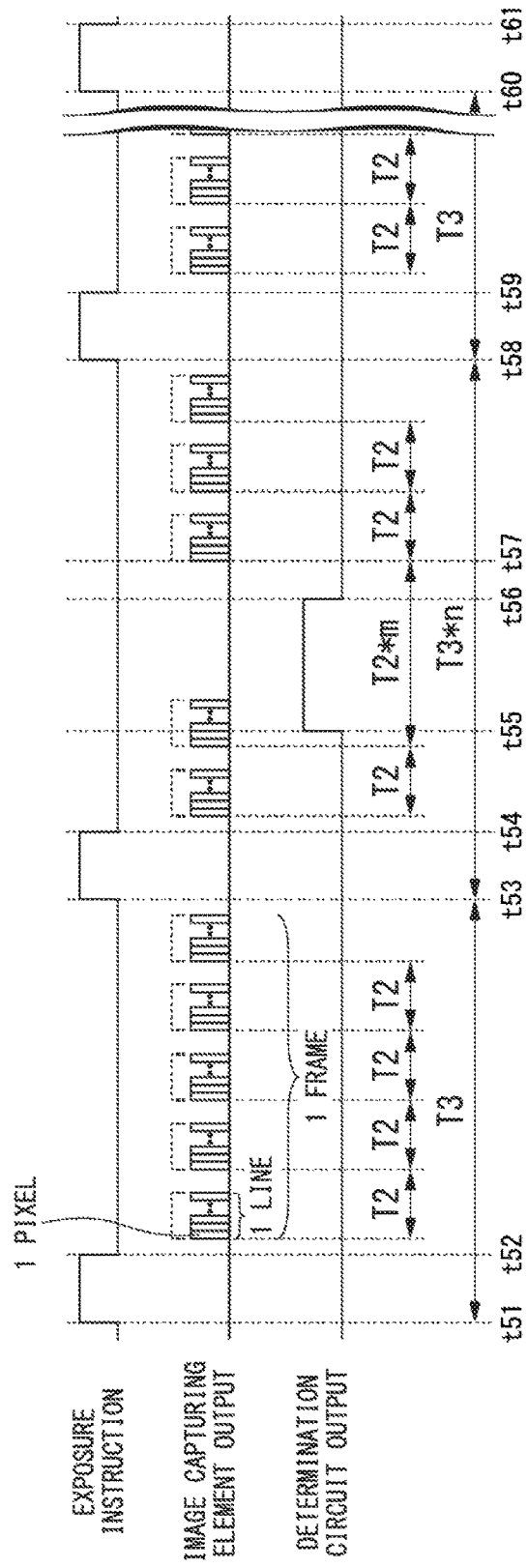
FIG. 13 is a timing chart showing timings at which the control circuit issues an exposure instruction to an image capturing element, timings at which the image capturing element outputs image data, and timings at which a determination circuit outputs a determination result according to the third embodiment of the present invention.

FIG. 13 is a timing chart showing timings at which the control circuit 106 outputs an exposure instruction to the image capturing element 101, timings at which the compression circuit 102 reads image data, and timings at which the determination result of the determination circuit 105 is output.

A description of operations the same as in the modification example of the second embodiment will be omitted. In the present embodiment, the control circuit 106 instructs the image capturing element 101 to perform exposure for one frame of image data and then the control circuit 106 instructs the compression circuit 102 to read image data. When an output stop instruction is not issued during one frame readout period, the control circuit 106 outputs an exposure instruction after a period of T3 has elapsed from an exposure start timing (t51 in the example shown) of the previous frame (t53 in the example shown).

On the other hand, when an output stop instruction is issued during one frame output period, the control circuit outputs an exposure instruction at a timing (t58 in the example shown) when an equation TE=T3*n (n is an arbitrary natural number) is fulfilled and later than an exposure start timing of the previous frame after the image data of the previous frame is output completely.

As described above, according to the present embodiment, the image capturing element 101 performs the process at a predetermined cycle. When reading of image data is stopped, the control circuit 106 instructs the image capturing element 101 to start exposure at a timing when the equation TE=T3*n (n is an arbitrary natural number) fulfilled from the exposure start timing of the previous frame. Accordingly, the compression circuit 102 can perform the compression process at a predetermined cycle such that the configuration of the compression circuit 102 can be simplified.

Moreover, even the configuration of the compression circuit 102 is simplified, when the compressed image data occupancy ratio of the transmission buffer 103 is high, the compression circuit 102 stops reading the image data on the basis of an output stop instruction. Accordingly, a situation that there is insufficient storage capacity in the transmission buffer 103 is prevented. Therefore, it is not necessary to increase the image compression rate even when the compressed image data occupancy ratio of the transmission buffer is high such that it is possible to transmit the compressed image data reliably while preventing a deterioration of image quality due to an increase in the image compression rate.

All or some of the functions of the respective units of the capsule endoscope 10 according to the above-described embodiments and the modification examples thereof and all or some of the functions of the respective units of the external terminal 20 according to the above-described embodiments and the modification examples thereof may be implemented by recording a program for implementing these functions on a computer-readable recording medium and causing a computer system to read and execute the program recorded on the recording medium. The "computer system" used herein may include an OS and hardware such as peripheral devices.

Moreover, the "computer-readable recording medium" refers to a portable medium such as a flexible disk, a magneto-optical disk, a ROM, or a CD-ROM, or a storage device such as a hard disk built into the computer system. Furthermore, the "computer-readable recording medium" may include a medium that dynamically holds the program for a short time, such as a communication link used for transmitting the program via a network such as the Internet or a communication line such as a telephone line, and a medium that holds the program for a certain period, such as a volatile memory inside the computer system serving as a server or a client in that case. In addition, the foregoing program may be used to implement part of the above-described functions, and may be used to implement the above-described functions in combination with a program already recorded in the computer system.

Although preferred embodiments of the present invention and the modifications thereof have been described, the present invention is hot limited to these embodiments and the modifications thereof. Elements may be added, omitted, substituted, and modified without departing from the spirit and scope of the present invention.

The present invention is not limited by the above-mentioned description, and is only limited by the appended claims.

What is claimed is:

1. A compressed image data transmitting device comprising:
    an image capturing element that captures images at a predetermined cycle and the image capturing element generates captured image data;
    a compression unit that dividedly reads one frame of the captured image data from the image capturing element a plurality of times and the compression unit performs a compression process on the captured image data to generate compressed image data;
    a transmitter that wirelessly transmits the compressed image data at a fixed bitrate;
    a transmission buffer that receives the compressed image data input from the compression unit, the transmission buffer stores the compressed image data, and the transmission buffer outputs the compressed image data to the transmitter;
    a determining unit that determines whether a compressed image data occupancy ratio is equal to or larger than a predetermined threshold value, the compressed image data occupancy ratio indicating a ratio of an area in which the compressed image data is being stored to an area of the transmission buffer in which the compressed image data is capable of being stored; and
    a control unit that instructs the compression unit to stop reading the captured image data when the compressed image data occupancy ratio is equal to or larger than the predetermined threshold value,
    wherein the compression unit generates the compressed image data according to a variable-length compression scheme in which fixed-length data is input and variable-length data is output,
    wherein the control unit instructs the image capturing element to perform an image capturing operation, and when the captured image data which has not been read from the compression unit is present in the image capturing element, the control unit instructs the image capturing element not to perform the image capturing operation, and the control unit subsequently instructs the image capturing element to perform the image capturing operation after the captured image data which has not been read from the compression unit is no longer present in the image capturing element,
    wherein the transmission buffer stores the compressed image data until the compressed image data is output to the transmitter such that new compressed image data is capable of being stored in a storage area in which the compressed image data was previously stored when the compressed image data is output to the transmitter,
    wherein the area of the transmission buffer in which the compressed image data is capable of being stored is an area in which an amount of data that is smaller than twice an amount of data that the compression unit reads at one time is capable of being stored, and
    wherein when the compressed image data occupancy ratio is equal to or larger than the predetermined threshold value and the reading of the captured image data has not been completed for predetermined lines of the image capturing element, the control unit delays a timing of stopping reading of the captured image data until the reading of the captured image data is completed for the predetermined lines.

2. The compressed image data transmitting device according to claim 1, wherein
    the control unit stops reading of the captured image data during a predetermined period from a timing when the compressed image data occupancy ratio is equal to or larger than the predetermined threshold value, and the control unit restarts reading of the captured image data after the predetermined period has elapsed.

3. The compressed image data transmitting device according to claim 1, wherein
    the control unit instructs the compress unit to perform the reading of the captured image data by the predetermined lines, the predetermined lines corresponding to the amount of data of the captured image data that the compression unit reads at one time.

4. The compressed image data transmitting device according to claim 3, wherein
    the control unit instructs the compress unit to perform the reading of the captured image data at a predetermined cycle.

5. The compressed image data transmitting device according to claim 4,
    wherein the image capturing element performs the image capturing operation at a fixed time periods, and
    wherein when the control unit stops reading of the captured image data during a period in which the compression unit reads one frame of the captured image data,
        the control unit stops the image capturing operation of the image capturing element at an image capturing timing according to the fixed time periods, and
        the control unit instructs the image capturing element to perform the image capturing operation at the image capturing timing which is an integer multiple of the fixed time periods after the reading of the one frame of the captured image data is completed.

6. A compressed image data transmitting and receiving system comprising:
    a compressed image data transmitting device; and
    a compressed image data receiving device,
    wherein the compressed image data transmitting device includes:
        an image capturing element that captures images at a predetermined cycle and the image capturing element generates captured image data,
        a compression unit that dividedly reads one frame of captured image data from the image capturing element a plurality of times and the compression unit performs a compression process on the captured image data to generate compressed image data,
        a transmitter that is wirelessly transmits the compressed image data at a fixed bitrate,
        a transmission buffer that, receives the compressed image data input from the compression unit, the transmission buffer stores the compressed image data, and the transmission buffer outputs the compressed image data to the transmitter,
        a determining unit that determines whether a compressed image data occupancy ratio is equal to or larger than a predetermined threshold value, the compressed image data occupancy ratio indicating a ratio of an area in which the compressed image data is being stored to an area of the transmission buffer in which the compressed image data is capable of being stored, and a control unit that instructs the compression unit to stop reading the captured image data when the compressed image data occupancy ratio is equal to or larger than the predetermined threshold value, wherein the compression unit generates the compressed image data according to a variable-length compression scheme in which fixed-length data is input and variable-length data is output, wherein the control unit instructs the image capturing element to perform an image capturing operation, and when the captured image data which has not been read from the compression unit is present in the image capturing element, the control unit instructs the image capturing element not to perform the image capturing operation, and the control unit subsequently instructs the image capturing element to perform the image capturing operation after the captured image data which has not been read from the compression unit is no longer present in the image capturing element, wherein the transmission buffer stores the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein when the compressed image data occupancy ratio is equal to or larger than the predetermined threshold value and the reading of the captured image data has not been completed for predetermined lines of the image capturing element, the control unit delays a timing of stopping reading of the captured image data until the reading of the captured image data is completed for the predetermined lines; and wherein the compressed image data receiving device includes a receiver that wirelessly receives the compressed image data from the compressed image data transmitting device at a fixed bitrate.

7. A compressed image data transmitting method comprising:

an image capturing step of capturing images at a predetermined cycle and generating captured image data by an image capturing element;

a compression step of dividedly reading one frame of the captured image data input from the image capturing element a plurality of times and performing a compression process on the captured image data to generate compressed image data by a compression unit;

a transmitting step of wirelessly transmitting the compressed image data at a fixed bitrate by a transmitter;

a transmission buffering step of receiving the compressed image data from the compression unit, storing the compressed image data, and outputting the compressed image data to the transmitter by a transmission buffer;

a determining step of determining whether a compressed image data occupancy ratio is equal to or larger than a predetermined threshold value by a determining unit, the compressed image data occupancy ration indicating a ratio of an area in which the compressed image data is being stored to an area of the transmission buffer in which the compressed image data can be stored; and a control step of instructing the compression unit, to stop reading the captured image data when the compressed image data occupancy ratio is equal to or larger than the predetermined threshold value by a control unit, wherein the compression step further includes a step of generating the compressed image data according to a variable-length compression scheme in which fixed-length data is input and variable-length data is output, wherein the control step further includes a step of instructing the image capturing element to perform an image capturing operation, and when the captured image data which has not been read from the compression unit is present in the image capturing element, instructing the image capturing element not to perform the image capturing operation and instructing the image capturing element to perform the image capturing operation after the captured image data which has not been read from the compression unit is no longer present in the image capturing element, wherein the transmission buffering step further includes a step of storing the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein during the control step, when the compressed image data occupancy ratio is equal to or larger than the predetermined threshold value and the reading of the captured image data has not been completed for predetermined lines of the image capturing element, a step of delaying a timing of stopping reading of the captured image data until the reading of the captured image data is completed for the predetermined lines is performed by the control unit.

8. A non-transitory medium saving program for causing a computer to execute:

an image capturing step of capturing images at a predetermined cycle and generating captured image data by an image capturing element;

a compression step of dividedly reading one frame of the captured image data input from the image capturing element a plurality of times and performing a compression process on the captured image data to generate compressed image data by a compression unit;

a transmitting step of wirelessly transmitting the compressed image data at a fixed bitrate by a transmitter;

a transmission buffering step of receiving the compressed image data from the compression unit, storing the compressed image data, and outputting the compressed image data to the transmitter by a transmission buffer;

a determining step of determining whether a compressed image data occupancy ratio is equal to or larger than a predetermined threshold value by a determining unit, the compressed image data occupancy ration indicating a ratio of an area in which the compressed image data is being stored to an area of the transmission buffer in which the compressed image data can be stored; and a control step of instructing the compression unit to stop reading the captured image data when the compressed image data occupancy ratio is equal to or larger than the predetermined threshold value by a control unit, wherein the compression step further includes a step of generating the compressed image data according to a variable-length compression scheme in which fixed-length data is input and variable-length data is output, wherein the control step further includes a step of instructing the image capturing element to perform an image capturing operation, and when the captured image data which has not been read from the compression unit is present in the image capturing element, instructing the image capturing element not to perform the image capturing operation and instructing the image capturing element to perform the image capturing operation after the captured image data which has not been read from the compression unit is no longer present in the image capturing element, wherein the transmission buffering step further includes a step of storing the compressed image data until the compressed image data is output to the transmitter such that new compressed image data is capable of being stored in a storage area in which the compressed image data was previously stored when the compressed image data is output to the transmitter, wherein the area of the transmission buffer in which the compressed image data is capable of being stored is an area in which an amount of data that is smaller than twice an amount of data that the compression unit reads at one time is capable of being stored, and wherein during the control step, when the compressed image data occupancy ratio is equal to or larger than the predetermined threshold value and the reading of the captured image data has hot been completed for predetermined lines of the image capturing element, a step of delaying a timing of stopping reading of the captured image data until the reading of the captured image data is completed for the predetermined lines is performed by the control unit.

* * * * *